(12) United States Patent
Winkler (10) Patent No.: US 9,597,231 B2
(45) Date of Patent: *Mar. 21, 2017

(54) TINNITUS TREATMENT

(71) Applicant: TIPA Tinnitus Corporation PTY LTD, Fairfield, NSW (AU)

(72) Inventor: Peter Anthony Winkler, Fairfield (AU)

(73) Assignee: TIPA Tinnitus Corporation PTY LTD. (AU)

( * ) Notice: Subject to any disclaimer, the term of this patent is extended or adjusted under 35 U.S.C. 154(b) by 290 days.

This patent is subject to a terminal disclaimer.

(21) Appl. No.: 14/055,914

(22) Filed: Oct. 17, 2013

(65) Prior Publication Data

US 2014/0046230 A1 Feb. 13, 2014

Related U.S. Application Data

(63) Continuation-in-part of application No. 12/525,126, filed as application No. PCT/AU2007/001960 on Dec. 19, 2007, now Pat. No. 8,579,796.

(30) Foreign Application Priority Data

Jan. 10, 2007 (AU) .............................. 2007900088

(51) Int. Cl.
| | |
|---|---|
| A61F 11/04 | (2006.01) |
| A61F 11/00 | (2006.01) |
| H04R 1/10 | (2006.01) |
| H04R 5/033 | (2006.01) |
| H04R 25/00 | (2006.01) |
| A61B 5/12 | (2006.01) |

(52) U.S. Cl.
CPC ............ *A61F 11/045* (2013.01); *A61F 11/00* (2013.01); *A61B 5/128* (2013.01); *H04R 1/10* (2013.01); *H04R 5/033* (2013.01); *H04R 25/75* (2013.01)

(58) Field of Classification Search
CPC ...................... H04R 25/75; A61M 2021/0027
USPC ................... 600/9–15, 25–58; 181/126–137; 381/23.1, 312–332; 601/46–48
See application file for complete search history.

(56) References Cited

U.S. PATENT DOCUMENTS 5,167,236 A * 12/1992 Junker ................. A61B 5/12
                                                600/559
6,377,693 B1 * 4/2002 Lippa et al. ................. 381/71.6
(Continued)

OTHER PUBLICATIONS

Franz B and Offutt G. Tinnitus Suppression with Threshold and Subthreshold sound stimuli. International Tinnitus Journal 9(1); p. 11-16, 2003.*

*Primary Examiner* — Catherine B Kuhlman
(74) *Attorney, Agent, or Firm* — Design IP (57) ABSTRACT

A method of treatment of the symptoms of tinnitus is disclosed in which a non-sinusoidal pulsating electric waveform having a pulse repetition rate (frequency) less than 100 Hz is applied to a headphone or an earphone or a like acoustic transducer worn by a tinnitus sufferer. Square, sawtooth and triangular waveforms are suitable. Preferably a sequence of square, triangular, square and square waveforms each of duration of 3 minutes, and separated by a silent pause of 10-15 seconds, is applied. Various devices for applying such waveform(s) to such transducers are disclosed including a clinical oscillator, an internet distribution system, a playback device, electronic or magnetic storage devices, and a cochlear implant.

19 Claims, 5 Drawing Sheets

(56) References Cited

U.S. PATENT DOCUMENTS 7,033,313 B2 4/2006 Lupin
2001/0051776 A1* 12/2001 Lenhardt .......................... 601/2

* cited by examiner

TINNITUS TREATMENT

FIELD OF THE INVENTION

The present invention relates to the treatment of tinnitus and, in particular, to the treatment of subjective tinnitus.

BACKGROUND OF THE INVENTION

Tinnitus is described as a ringing or similar sensation of sound in the ears. It is a conscious expression of a sound that originates in an involuntary manner in the head of a person, or appears to do so. It is often associated with other hearing difficulties, but may present alone.

Tinnitus is classified into two types known as objective tinnitus and subjective tinnitus. Objective tinnitus is a rarer form and consists of head noises audible to people other than the sufferer. The sounds are generally external to the auditory system and many be caused by repetitive muscle contractions or inner ear structural defects.

The more common subjective tinnitus is much less understood. Sounds heard by sufferers can range from a metallic ringing, buzzing, popping or non-rhythmic beating sounds. The origins of this kind of tinnitus are as yet unclear. This is quite a distressing condition and prevents some sufferers from leading a fulfilling life. Antidepressants are commonly used to alleviate the distress felt because of the condition but do not stop the tinnitus. Various treatments have been tried to alleviate or cure tinnitus and have either been unsuccessful or have unproven results. Medications have proven unsuccessful.

A common treatment involves the use of tinnitus maskers together with counseling. Masking is the phenomenon whereby tinnitus is not perceived while another sound is presented to the sufferer's ear. Thus, the masking sound replaces the tinnitus sound. The masking sound is generally white noise, usually intermingled sine waves between 400 Hz and 10,000 Hz having a substantially flat frequency spectrum (that is many frequencies are present each to a substantially equal extent). Masking has also been attempted using music.

Hearing aids which increase normal speech above the level of the tinnitus may assist with a sufferer's hearing; however, these do not remove the tinnitus. In addition to assisting with hearing, the aids can introduce white noise to the ear(s) of the sufferer, thereby providing some masking.

Tinnitus retraining therapy is another treatment method which uses low volume white noise generators over a prolonged period of time in attempting to produce a less stressful response to the tinnitus. This approach is as yet unproven.

Alternative therapies used by some practitioners include prescribing herbal medications such as Gingko Biloba; and the use of acupuncture; hypnosis; electrical stimulation and bio-feedback. None of these treatments have shown any lasting effects.

To date, there has been no therapeutically successful treatment of tinnitus in terms of producing medium or long term remission.

It has previously been observed in tinnitus patients that there can be a brief period when tinnitus is absent or reduced after a masking signal ceases. This absence or reduction of tinnitus is called residual inhibition.

Residual inhibition usually lasts only a few seconds at the most. Because it is so short lived, it has previously been disregarded as being therapeutically useful. Attention to residual inhibition is actively avoided in current masking therapy.

Cochlear Implants (CI) have been noted to reduce tinnitus in some sufferers. The tinnitus is reduced while the cochlear implant is switched on and this constitutes masking Residual inhibition has not been regularly demonstrated in sufferers having cochlear implants. Some sufferers have developed tinnitus for the first time after the cochlear implant has been implanted. Utilizing a cochlear implant is not a recommended treatment for tinnitus.

One worker in the field (Zeng Fan-Gang) is reported to have implanted a cochlear implant in one ear of a patient with normal hearing but severe suicidal tendencies induced by the symptoms of tinnitus. Cochlear implants generally destroy the normal hearing of the patient's implanted ear. The cochlear implant was used to provide masking. Low frequency modified sine waves were applied to the cochlear implant. There was some initial alleviation of the patient's symptoms, however, the patient did not experience residual inhibition and subsequently suffered from tinnitus rebound. So the presumed loss of hearing in one ear did not improve the patient's symptoms over time.

Residual inhibition can be described as complete, partial or rebound. In complete residual inhibition the tinnitus is totally absent after the cessation of the masking sound. In partial residual inhibition the tinnitus is reduced in intensity but still present after the cessation of the masking sound. In rebound residual inhibition the tinnitus can be louder after the cessation of the masking sound. It is common for initial complete residual inhibition to give way to subsequent partial residual inhibition if the tinnitus gradually returns.

In fact, residual inhibition is not sought or utilized as part of current tinnitus masking therapies. Jack Vernon, a founding father of masking therapy, states in his book *Tinnitus diagnosis/treatment* (Abraham Shulman publisher) at page 62: "Often, tinnitus patients tell us they cannot see the point of masking: "Why trade one sound for another?" Then we demonstrate masking, and often the patient immediately understands how it alone can produce relief. In the first place, a band of noise is aesthetically more acceptable than a high-pitched shrill tone. Second, outside sound can be ignored more easily than can the tinnitus. Despite this, however, many patients are overly impressed with the demonstration of residual inhibition. For some it represents the first time since its inception that they have not heard their tinnitus. Regardless of its temporary nature, they still expect a permanent residual inhibition to develop. We explain that masking is successful when it alone is the relief and that residual inhibition is not the goal of masking. Despite all these disclaimers, we have encountered clinicians who have recommended no masking because the patient did not display residual inhibition in the clinical test. We have also seen patients who would not continue the use of masking simply because they obtained no residual inhibition. In either of these situations, improper information and expectations have been conveyed" (emphasis added).

The inventor has treated tinnitus sufferers in his private clinic as an otologist for over 30 years.

Genesis of the Invention

The genesis of the present invention is to provide relief to tinnitus sufferers which is prolonged beyond that momentarily provided by residual inhibition.

The different approach of the present invention is based on the inventor's insight that if the duration of residual inhibition could be prolonged from seconds and minutes to hours or days, it would be a potent therapeutic tool. Further, that more prolonged residual inhibition would constitute long term remission of tinnitus and therefore a "cure". This is a marked departure from the prior teachings.

SUMMARY OF THE INVENTION

According to a first aspect of the present invention there is disclosed an internet based system for the acoustic treatment of tinnitus, said system comprising a website hosted by an internet service provider, a payment acceptance facility associated with said website, and an acoustic signal associated with said website, wherein a sufferer of tinnitus can access said website via the internet, provide an accepted payment and download said acoustic signal to a headphone or a like acoustic transducer and associated with at least one ear of said sufferer and wherein said acoustic signal comprises a non-sinusoidal pulsating electric waveform having a pulse repetition rate less than 100 Hz.

According to a second aspect of the present invention there is disclosed a method of treatment of tinnitus, said method comprising the steps of:

applying a headphone, earphone, or like acoustic transducer to at least one ear of a tinnitus sufferer, applying only an acoustic signal to said headphone, earphone or acoustic transducer, said acoustic signal being without any white noise, ultrasonic, or radiofrequency component or carrier, and said acoustic signal comprising a non-sinusoidal pulsating electric waveform having a pulse repetition rate less than 100 Hz.

According to a third aspect of the present invention there is disclosed an electrical generator for the treatment of tinnitus, said generator comprising at least one oscillator means to generate a non-sinusoid pulsating electric waveform having a pulse repetition rate no greater than 100 Hz, and an output connection adapted to connect with a headphone or like acoustic transducer.

According to a fourth aspect of the present invention there is disclosed a method of treatment of tinnitus, said method comprising the steps of:

applying a headphone, earphone, or like acoustic transducer to at least one ear of a tinnitus sufferer, applying only an acoustic signal to said headphone, earphone or acoustic transducer, said acoustic signal being without any white noise, ultrasonic, or radiofrequency component or carrier, and said acoustic signal comprising a non-sinusoidal pulsating electrical waveform having a pulse repetition rate less than 100 Hz.

According to a fifth aspect of the present invention there is disclosed an electrical generator for the treatment of tinnitus, said generator comprising at least one oscillator means to generate a non-sinusoid pulsating electric waveform having a pulse repetition rate no greater than 100 Hz, and an output connection adapted to connect with a headphone or like acoustic transducer.

According to a sixth aspect of the present invention there is disclosed an electrical playback device for the treatment of tinnitus, said device comprising an electronic or magnetic storage means in which is stored a non-sinusoidal pulsating electric waveform having a pulse repletion rate less than 100 Hz, and an output connection adapted to connect with a headphone or like acoustic transducer.

According to a seventh aspect of the present invention there is provided a stored audio product for the treatment of tinnitus, said product comprising an electric or magnetic storage means in which is stored a non-sinusoidal pulsating electric waveform having a pulse repletion rate less than 100 Hz, said product when actuated in a compatible electrical playback device reproducing said waveform in a form acceptable to a headphone or like acoustic transducer.

According to the eighth aspect of the present invention there is disclosed a cochlear implant including a processor unit and an implantable electrode connected to said processor unit to receive a voltage therefrom, said processor unit being programmed to receive or generate a non-sinusoidal pulsating electric waveform having a pulse repetition rate less than 100 Hz which is applied to said implantable electrode.

The inventor initially discovered that non-sinusoidal pulsating electric waveforms such as square waves of a pulse repetition rate (or loosely "frequency"—being the reciprocal of the waveform's repetition period) less than 100 Hz (and preferably in the range of 10-100 Hz) produced significantly longer residual inhibition in many volunteers. Subsequently, it was observed that a sequence of differing non-sinusoidal pulsating waveforms was even more effective, producing complete residual inhibition for up to 24 hours. Moreover, it has been discovered that the sequence can be re-applied before the tinnitus returns, to extend the period of residual inhibition for at least some patients to several days.

Again, re-application of therapy before the tinnitus symptoms reappear was avoided by experts in the field such as Vernon.

Furthermore, non-sinusoidal pulsating electric waveforms such as square, triangle and sawtooth waves have not been used in masking therapies. For example, Vernon goes so far as to say that it is likely that low frequency sounds amplified by a hearing aid interfere with the production of residual inhibition.

The intensity of the masking signal is discussed in the book *Tinnitus* (published by Churchill Livingstone) written by Jonathan Hazell at page 83. Dr Hazell is a founding father of the currently favored method of treatment known as retraining therapy, as follows: "For the most part, the lower the intensity of the masking sound (while still effectively covering the tinnitus), the more readily it is accessed as a substitute for the tinnitus. Always keep in mind that masking, in any of its forms, is only a substitution of an external sound for the internal one." And later at the same page "that survey also showed that the majority of patients displaying either CRI (complete residual inhibition) or PRI (partial residual inhibition) do so for less than one minute."

The mechanism(s) by which low frequency non-sinusoidal pulsating waveforms (and the synergistic effect of sequential differing waveforms) produce prolonged residual inhibition are not known. The discovery of such synergy is a significant departure from previously known physiology or theory relating to tinnitus mechanisms. Such synergy is likely to be a useful research tool to investigate tinnitus physiology as well as providing a therapeutic method. Synergy is a recognized biological response in the interaction of pharmaceutical agents. It is accordingly the inventor's hypothesis that the therapeutic sound signals are acting at a biochemical level mediated by neurotrophin like substances released at the cochlear/auditory nerve interface (spiral ganglion) in response to the signal.

The present invention accordingly allows tinnitus sufferers some relief from their condition in a way that provides a significant advantage over existing alternatives.

BRIEF DESCRIPTION OF THE DRAWINGS

Various embodiments of the present invention will now be described with reference to the drawings in which.

DETAILED DESCRIPTION OF THE PREFERRED EMBODIMENTS

The ensuing detailed description provides preferred exemplary embodiments only, and is not intended to limit the scope, applicability, or configuration of the invention. Rather, the ensuing detailed description of the preferred exemplary embodiments will provide those skilled in the art with an enabling description for implementing the preferred exemplary embodiments of the invention. It being understood that various changes may be made in the function and arrangement of elements without departing from the spirit and scope of the invention, as set forth in the appended claims.

As used in the specification and claims, the term "acoustic transducer" means any device that generates sound waves from an electrical signal. Examples of acoustic transducers include, but are not limited to, headphone and earplugs.

Figure 1:
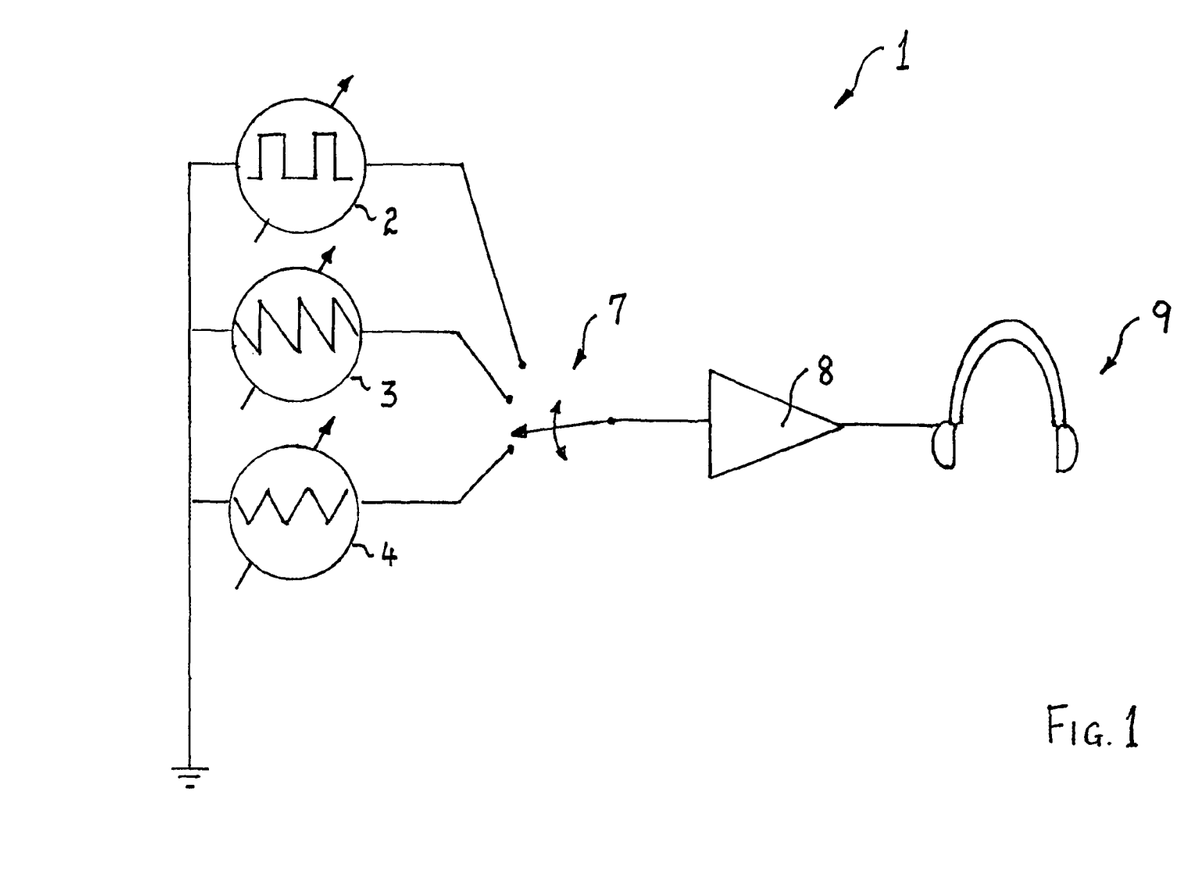
FIG. 1 is a schematic electric circuit block diagram of an electrical generator apparatus which is particularly useful for clinical work.

As seen in FIG. 1, a signal generator 1 useful for clinical evaluation is illustrated having three oscillators in the form of a square wave oscillator 2, a sawtooth oscillator 3, and a triangular wave oscillator 4. Each of the oscillators 2-4 is illustrated with an inclined arrow to indicate that the pulse repetition rate (frequency) is adjustable (preferably in the range of 10-100 Hz). In relation to the square wave oscillator 2 the mark: space ratio is also adjustable.

The output of each of the generators is connected via a selector switch 7 to an amplifier 8, the output of which is connected to a pair of headphones 9.

Figure 2:
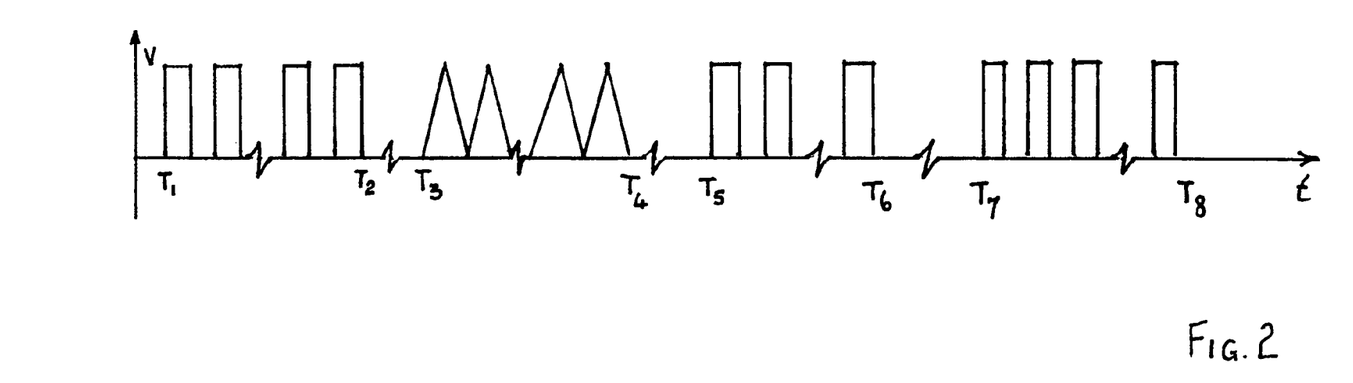
FIG. 2 is a graph of the voltage waveforms of function of time applied to the head phones of FIG. 1, the time axis being truncated.

Turning now to FIG. 2, a preferred voltage applied to the headphones 9 as a function of time is illustrated. In the preferred arrangement, a square wave is applied for a first period commencing at time $T_1$ and ceasing at time $T_2$. Then there is a pause for a first duration extending between time $T_2$ and $T_3$ at which time a triangular waveform is applied which ceases at time $T_4$. Then there is a further pause of a second duration which ceases at time $T_5$ at which time a second square wave is applied until time $T_6$. Then there is a further pause of a third duration which ceases at a time $T_7$ at which time a third square wave is applied until time $T_8$, at which stage the signal to the headphones ceases. It is preferable that each of the electrical signals generated by the each oscillator 2, 3, 4 and supplied to headphones 9 consist only of the desired acoustic waveform. In other words, the electrical signals are preferably substantially free of any sinusoidal waves, white noise, ultrasonic waves, radio frequency waves, radio frequency carrier, or ultrasonic carrier.

The preferred values and range of values for the above-mentioned intervals are set out in Table 1 below:

TABLE 1

| Interval | Preferred Value | Range |
| --- | --- | --- |
| First Period $T_2$-$T_1$ | 3 Minutes | 1-20 Minutes |
| First Duration $T_3$-$T_2$ | 10-15 Seconds | Zero-5 Minutes |
| Second Period $T_4$-$T_3$ | 3 Minutes | 1-20 Minutes |
| Second Duration $T_5$-$T_4$ | 10-15 Seconds | Zero-5 Minutes |
| Third Period $T_6$-$T_5$ | 3 Minutes | 1-20 Minutes |
| Third Duration $T_7$-$T_6$ | 10-15 Seconds | Zero-5 Minutes |
| Fourth Period $T_8$-$T_7$ | 3 Minutes | 1-20 Minutes |

Figure 3:
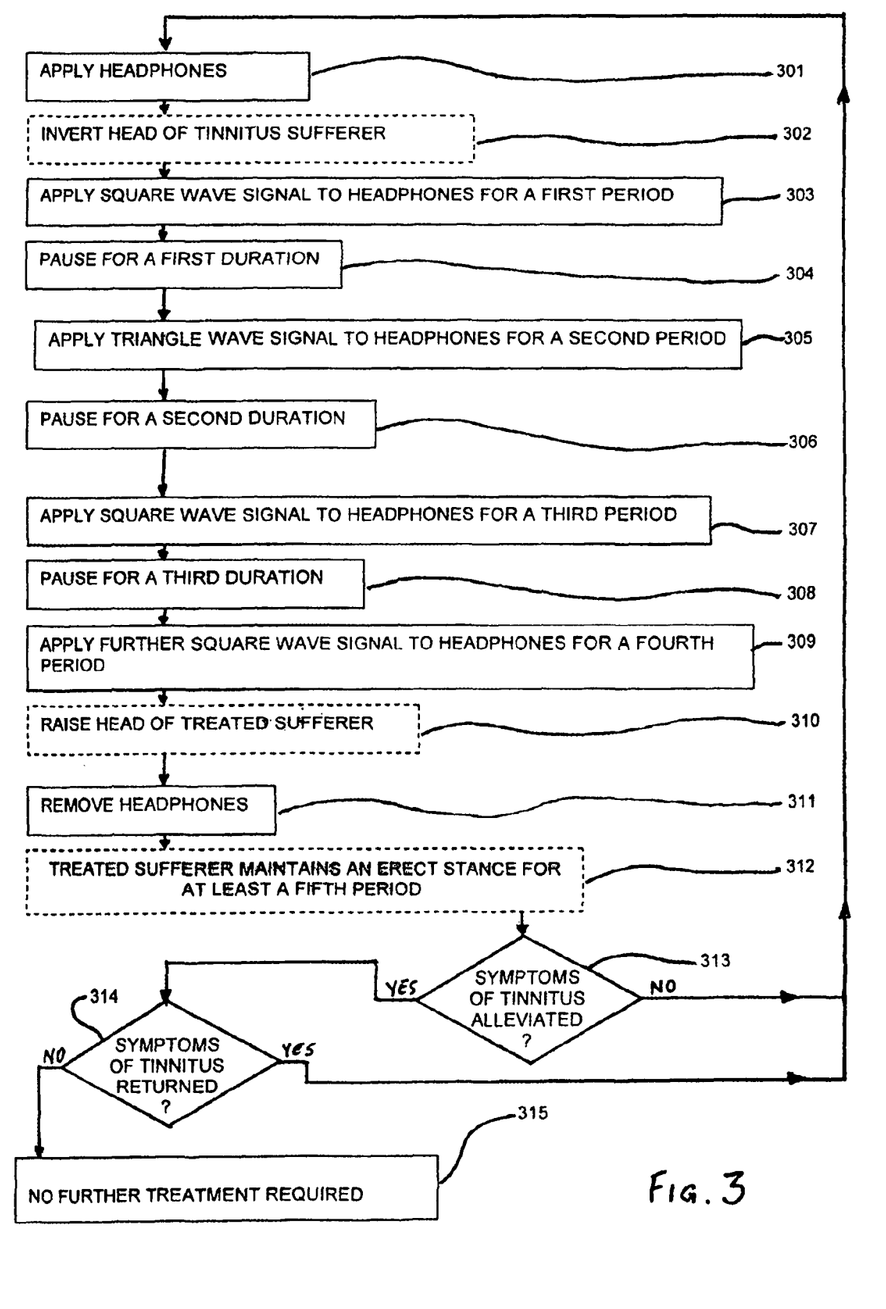
FIG. 3 is a flow chart illustrating the steps of a preferred sequence of treatment.

Turning now to FIG. 3, the various steps carried to treat a tinnitus sufferer are illustrated in flow chart form. Those steps in boxes having a dashed outline are optional steps and in accordance with one embodiment of the present invention need not be included. The first step is step 301 which is applying the headphones 9 to the ears of the tinnitus sufferer whilst in the conventional upright sitting position.

If desired, as indicated by step 302, the head of the tinnitus sufferer can be inverted. This is most easily done by allowing the tinnitus sufferer to lie face downwards on a horizontal surface such as a bed with the head projecting beyond the end of the bed which then enables the neck to be comfortably bent so as to invert the head (i.e., so that the forehead is below the chin).

Then in a succession of steps 303-309, the voltage waveform indicated in FIG. 2 is applied to the headphones 9. Thereafter, if step 302 has been carried out, then step 310 is carried out so as to raise the head of the treated sufferer. Then as indicated in FIG. 3 at step 311 the headphones are removed. Where the head has been inverted then the treated sufferer as indicated at step 312 maintains an erect stance for at least a fourth period which is in the rage of from approximately 5 minutes to approximately 60 minutes and preferably approximately 20 minutes. In this connection it is desirable that the treated sufferer avoid bending over so as to tie their shoe laces, for example.

As indicated in the decision box 313, if the symptoms of tinnitus have been alleviated and as indicated in decision box 314 if the symptoms of tinnitus do not return, then no further treatment is required as indicated in step 315. However, in the event that the symptoms of tinnitus are not alleviated or do return, then further treatment should be undertaken after a suitable interval (e.g. approximately 1 hour—several days or even weeks) and steps 301 and following are again undertaken.

Significant enhancement of the effect of the signal by adopting a head down prone position has been observed. This is not inconsistent with the neurotrophin theory or hypothesis referred to above. The head down position may enhance neurotrophin release by increased cerebrospinal fluid (CSF) pressure, and/or altered cochlear blood flow, and/or gravitational effect upon particulate matter in the cochlear apical turn.

Figure 4:
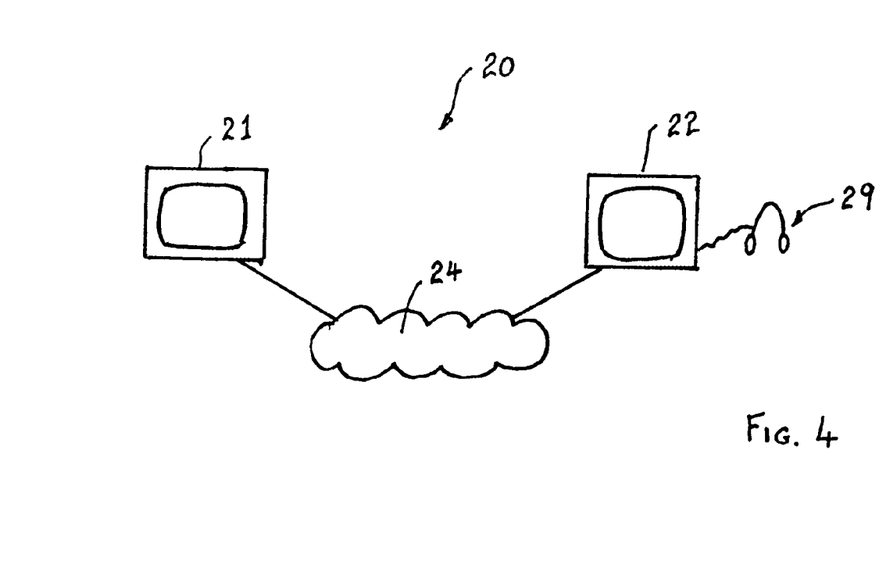
FIG. 4 is a schematic representation of an internet based system for delivering an audio signal to tinnitus sufferers suitable for treating tinnitus symptoms.

Modern technology enables acoustic signals to be applied to human ears in many and varied different forms. FIG. 4 illustrates in schematic fashion an internet based system 20 of distributing a suitable treatment signal. A computer 21 operated by an internet service provider (ISP) is loaded with a website of substantially conventional nature in which are located (i) various instructions to be followed by a tinnitus sufferer,
(ii) a conventional payment acceptance mechanism which can accept payment from a tinnitus sufferer by means of, for example, a credit card or debit card, again of conventional nature, and
(iii) most importantly and in accordance with the disclosure of the present application, a stored electrical waveform of the type illustrated in FIG. 2

A computer 22 operated by a tinnitus sufferer and equipped with headphones 29 such as are used with computer telephony, the downloading of audio or video clips, and the like, is able to access the webpage contained within the computer 21 by means of the internet 24.

Thus the tinnitus sufferer, after logging on to the appropriate website, authorizes a credit card payment, places the headphones 29 on the ears and thereby receives via the internet 24 the acoustic waveform illustrated in FIG. 2, or similar. This is substantially analogous to paying for and downloading, a ring tone, song, piece of music or the like except, of course, that the consequences for the tinnitus sufferer are vastly different.

Figure 5:
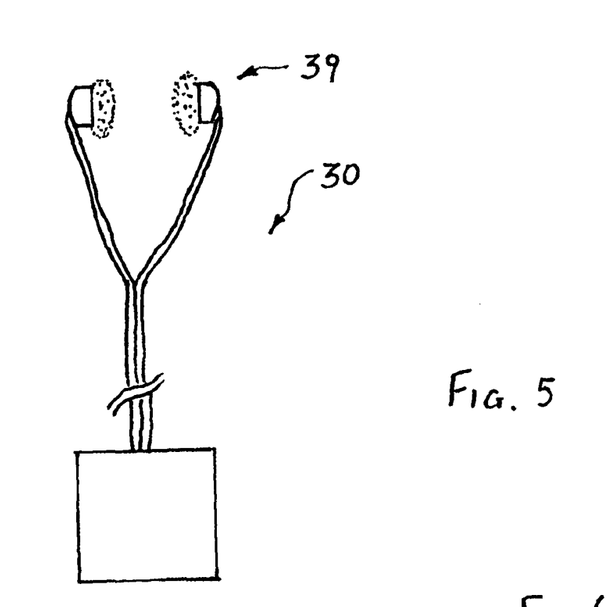
FIG. 5 shows in schematic form a playback device such as a WALKMAN, DISCMAN, or I-POD (all Registered Trademarks)

Another way of treating tinnitus sufferers is illustrated in FIG. 5 where a playback device 30 having a pair of earphones or earplugs 39 is illustrated. Such playback devices 30 are well known and are sold under the registered trademarks WALKMAN, DISCMAN and I-POD, for example.

Figure 6:
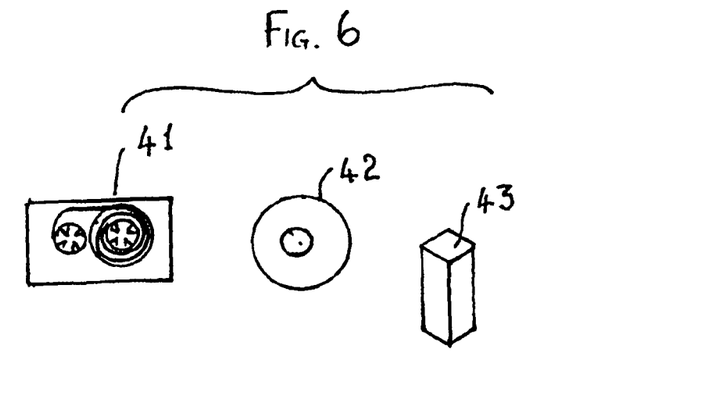
FIG. 6 illustrates various electronic or magnetic storage media useful for storing acoustic signals.

FIG. 6 illustrates electronic or magnetic storage devices able to be used with the playback device 30 of FIG. 5 in the form of a magnetic tape cassette 41, a compact disc 42 or solid state data storage memory device 43.

It will be understood by those skilled in the electrical engineering arts that the non-sinusoidal pulsating waveforms generated by the oscillators 2, 3 and 4 in FIG. 1 are rich in harmonic frequencies. As a consequence, not all audio devices appear to be able to adequately convey the acoustic energy to the ear or ears of the tinnitus sufferer. This may be due to lack of bandwidth or an inappropriate frequency response, or in some cases due to analogue-to-digital or digital-to-analogue conversion, data compression, or the like. The precise reason for this inability of some device(s) to perform adequately is relatively unimportant since it is a simple matter to test a particular device to see whether or not it operates satisfactorily. Those devices which do not operate satisfactorily are simply discarded from further consideration. For example, AKG 55 headphones and the earplugs sold with I-POD devices had been found not to work.

The preferred magnitude of the voltage illustrated in FIG. 2 is that required by the transducer to produce an acoustic output which in a sufferer provides a minimum masking level. For some sufferers with normal hearing this acoustic output approaches approximately 80 dB. For those sufferers with impaired hearing an even higher level may be required. Accordingly, the acoustic output at which a minimum masking level is achieved is a relatively high level of intensity at the ears of the tinnitus sufferer. For example, this perceived volume level is well above the level of normal speech or levels at which music are listened to by those of normal hearing. For this reason, conventional loud speakers are not a very suitable acoustic transducer for use in the treatment of tinnitus sufferers (and an opposed pair of sub-woofer speakers is not a very convenient piece of apparatus). Instead, headphones or earphones are generally much more convenient. Furthermore, it is thought that therapeutic effects are achieved by sound which reaches the interior of the head of the sufferer by means other than the conventional ear, such as the bone of the skull to the rear of the ear. For this reason, headphones are to be preferred. The preferred headphones are those manufactured by SENNHEISER of Germany and Model HD256 Linear, in particular.

The treatment may be applied at a clinic at regular appointments. Alternatively, the acoustic signal can be put on a device or recording (as discussed above in relation to FIGS. 5 and 6) which the tinnitus sufferer can carry with them and use when necessary, or as instructed by the therapist, to treat the tinnitus. The device can have an appropriate control to choose the volume or intensity, and other parameters, of the applied signal. The acoustic signal can also be delivered via the internet, as discussed above in relation to FIG. 4. The acoustic signal can further be included as part of a hearing aid, a device worn behind the ear or in an implant within the ear.

Figure 7:
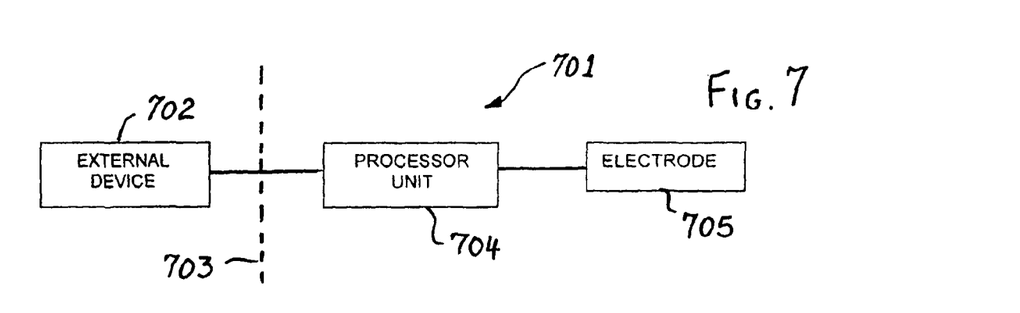
FIG. 7 is a schematic block diagram of a cochlear implant.

In this connection a hybrid cochlear implant which includes a short electrode implanted into the basal turn of the cochlear only, is used for some persons to treat high tone hearing loss whilst preserving the relatively normal low tone hearing. Such a cochlear implant can include automatic tinnitus suppression in addition to the regular hearing facility. Such a cochlear implant can deliver the desired acoustic energy in either one of two ways. In the first way, the microphone associated with the implant receives the acoustic energy and converts it into a first electrical signal. The processor protocol within the cochlear implant converts the first electrical signal into a second electrical signal which is actually applied to the cochlea. In the second way, software within the implanted processor can be programmed to generate the desired electrical signal. Such a cochlear implant 701 is illustrated schematically in FIG. 7 with an external device 702, for example including a microphone and a re-charging means or energy source, located outside the skin 703. Inside the skin 703 are the processor unit 704 and electrode 705. This system can also be used in a conventional cochlear implant in an ear with no residual hearing.

Treatment in acoustic or electrical form may be applied to the ipsilateral (same side) or contralateral ear (opposite side) in the event that symptoms appear in one ear only, or both ears, as appropriate.

In the preferred form, the therapist must additionally select a sequence of multiple signals, as well as the waveform type and pulse repetition rate for each signal in the sequence. In practice, it is preferred that the sequence be selected first. It has been found most effective in trials to use different shaped waveforms, having small differences between the frequencies, for example 0.5 to 1.0 Hz at around 30 Hz. Thus, selection of the sequence and the first waveform to some extent limits the variables for the other signals in the sequence. In the sequential delivery, it is preferred that the subsequent signals are provided reasonably soon after the preceding ones. A 10-15 second delay was used on Volunteer #6 as described below, for example.

An initial six case studies discussed below show how real sufferers of tinnitus have been provided with practical and inexpensive assistance to obtain more than merely momentary relief from tinnitus symptoms.

Case Study Volunteer #1

The first case study involved a 67 year old female who developed constant unremitting tinnitus in the right ear.

She had normal hearing which was unusual for her age. The tinnitus was sometimes pulsatile and sometimes continuous but always present. Carotid Doppler showed plaque in the carotids but normal flows and a magnetic resonance imaging (MRI) scan of the brain was normal.

On initial assessment she had 7 hours of complete residual inhibition after initial testing with a 60 Hz sawtooth wave in the right ear. She was then treated weekly with this signal in both ears for 10 minutes at each visit. The period of complete residual inhibition became longer after each treatment.

A further two months later she reported 72 hours of complete residual inhibition and said that she no longer heard her tinnitus during the day.

After another fortnight tinnitus was present but she said that tinnitus had been absent all week.

One week later when she arrived for treatment there was no tinnitus present.

She was asked to return if the tinnitus reappeared and has not returned for any treatment. She is therefore presumed to be "cured".

Case Study Volunteer #2

A 74 year old male complained of constant unremitting tinnitus in his left ear which had been present for nine years. His audiogram showed a small bilateral high tone sensory loss consistent with presbycusis. The hearing loss was a little worse in the left ear. A CT scan of the brain was normal.

At the initial assessment, he achieved complete residual inhibition following a three minute exposure to a 44 Hz square wave signal applied to the left ear.

Arrangements were made to him to return for weekly treatment, however, he called to say that his tinnitus had not returned and that he was very pleased with the treatment. He was asked to return if the tinnitus reappeared. Two months later he was phoned and he again reported no tinnitus. He has not been heard from since and is therefore presumed to be "cured".

Case Study Volunteer #3

A 29 year old male developed left sided tinnitus after walking behind a jet engine on the tarmac at Sydney Airport. He has normal hearing. The tinnitus was interfering with his ability to work.

Three weeks after walking behind the jet engine, the tinnitus had not subsided as initially expected and was still interfering with his work. After three minutes of 27 Hz square wave applied to the left ear he had 50% partial residual inhibition.

This was followed by three minutes of stimulation with a 20 Hz square wave which produced complete residual inhibition.

The tinnitus has not returned since.

Case Study Volunteer #4

A 44 year old female complained of constant unremitting tinnitus in the right ear which had been present for six months. She was a non-English speaking European immigrant. Her husband interpreted for her.

She had not responded to treatment with Serc or Rivotril (both Registered Trade Marks) and an MRI/MRA scan of her brain was normal. Her audiogram was within normal limits.

Two months after this initial drug treatment, she was treated with a 27 Hz square wave in the right ear. This produced complete residual inhibition which has persisted.

Case Study Volunteer #5

A 62 year old male had one of the worst cases of bilateral tinnitus the inventor has seen. He was a diabetic and has had coronary artery bypass grafts twice. The tinnitus in his left ear is so loud that he can hear it clearly above the noise of jet engines when sitting in the back of a plane. He is psychologically well adjusted and copes with the tinnitus but does not like it.

The tinnitus is constant and unremitting and although present for several years it has become louder recently.

His audiogram showed a bilateral sensory loss of 30-40 dB at all frequencies.

He has had specialist neurological assessment including an MRI brain scan which was normal. He has previously been seen by an ear, nose and throat (ENT) specialist (other than the inventor) for his tinnitus, and without success.

He has been tested with a multiplicity of signals across the whole frequency/pulse repetition rate spectrum by the inventor. Many hours have been spent working with him.

He was stimulated with 60 Hz and 80 Hz square waves for five minutes binaurally which has produced complete residual inhibition in the right ear and 50% partial residual inhibition in the left ear. A more effective response was obtained at a stimulation of 27 Hz for 3 minutes. The symptoms of tinnitus are presumed not to have returned since the very pleased volunteer has not returned for any treatment or follow-up.

Case Study Volunteer #6

A 42 year old male health care worker had constant unremitting bilateral tinnitus which had been present for 30 years and caused significant sleep disturbance. He had normal hearing and normal MRI/MRA scans of brain.

Over a six month period, he was assessed on a weekly basis and treated with a multiplicity of signals applied binaurally using headphones. It was during this process that the discovery of a synergy between sequential applications of different signals was made.

Using three different signals (X, Y & Z) of three minutes duration each applied in sequence XYXZ with a 10-15 second gap between the signals, the volunteer experienced 24 hours of complete residual inhibition. The same response was obtained every time he was exposed to a signal.

Furthermore, when the signal was applied before the tinnitus returned, an additional 24 hours of complete residual inhibition was achieved. A period of tinnitus absence of 5 days was achieved using daily signal exposure. The volunteer now uses this signal pattern on a regular basis to turn his tinnitus off.

Trials with this volunteer have established that none of the signals can produce this level of residual inhibition when used in isolation. Removing one of the signals from the sequence prevents long term residual inhibition from developing. For example, signal X applied for four periods each of 3 minutes (12 minutes in total) produces only 60% residual inhibition; signal Y for four periods each of 3 minutes (12 minutes in total) produces only 40% residual inhibition; and signal Z for four periods each of 3 minutes (12 minutes in total) also produces only 40% residual inhibition (as reported by the volunteer).

Thus, it is clear that synergy is occurring between the different signals, as a superior level of inhibition is obtained from the sequence compared to any of the components.

The signals are:

X a 27.5 Hz square wave produced by a digital synthesizer.

Y a 28 Hz triangle wave produced by the same digital synthesizer.

Z a 28 Hz square wave produced by a different digital sound generator.

The three above-mentioned signals were created by software associated with a Macintosh computer which was connected to a DIGI002 manufactured by DigiDesign of the USA which functioned as a console panel to which the headphones were connected. The Macintosh computer included a PROTOOLS program the internal signal generator of which was used to produce the Z waveform directly. In addition the Macintosh computer included a plug-in suite of programs known as REASON which includes a SUBTRACTOR synthesizer sub-program. The X waveform referred to above was generated using this sub-program and selecting a musical tone being the fourth octave below middle A. This represents a pulse repetition rate of 27.5 Hz. In order to create the Y waveform the "frequency" used for the X waveform was increased by "2 cents" or 2%. Since 1.02 times 27.5 equals 28.05, this resulted in the Y waveform having a pulse repetition rate of 28 Hertz.

Figure 8:
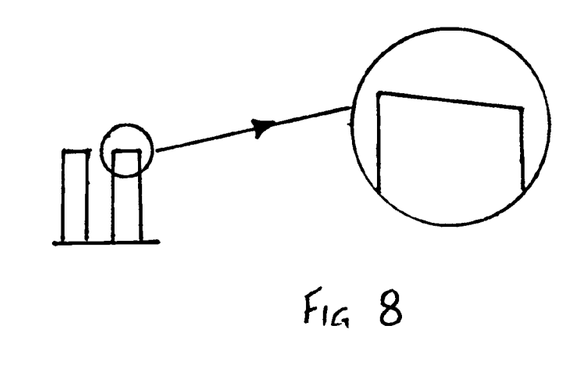
FIG. 8 is an enlarged view of the top of the X square wave.
Figure 9:
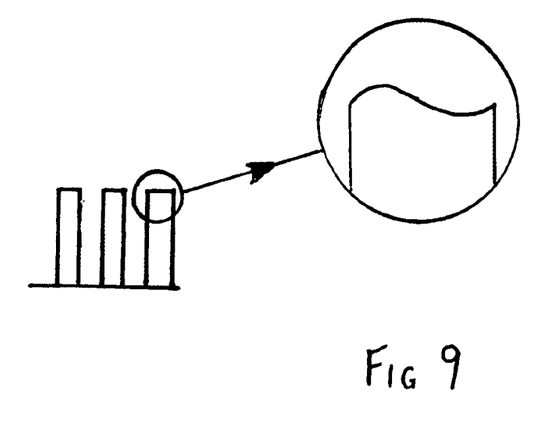
FIG. 9 is an enlarged view of the top of the Z square wave.

The uppermost portions of the X and Z square waveforms are illustrated in FIGS. 8 and 9 respectively. The X waveform shows a slight droop in its top compared to what ideally should be a flat or horizontal portion of the waveform. Such droops are well known in waveforms generated with circuit oscillators as a result of a slow exponential decay of a capacitor voltage. The Z the waveform also did not have a flat or horizontal top portion as one would expect but instead shows a sinusoidal fluctuation the period of which exactly equals the on time of the on/off square wave. This artifact is probably caused by the way in which the square wave is generated by means of the computer program referred to above.

Furthermore, when this volunteer was treated with his head inverted, a substantial prolongation of the period of residual inhibition was experienced.

After the initial complete residual inhibition usually experienced by this volunteer when treated in a seated position with the head upright, a prolonged and significant partial residual inhibition occurred. The total duration of inhibition was five days after one 12 minute exposure. This response was repeatable.

Following the successful results with volunteer #6, a pilot study was conducted on a further 19 volunteers who presented to the inventor with long term unremitting tinnitus which had not responded to any other treatment. Of these 19 volunteers, 10 had a response which was considered therapeutic. A therapeutic response was considered to be residual inhibition (RI) of 50% or greater and lasting for at least 3 hours or longer. It is to be noted that an RI of 60% means that the volunteer's tinnitus has been reduced to 40% of its original loudness.

These results are summarized below:

The volunteers are numbered 6.1 through 6.19. All volunteers were given the XYXZ procedure of 3 minutes per signal—a total of 12 minutes of sound exposure. The signal was applied by headphones to both ears at the MML (minimum masking level). There was no inversion of the head.

6.1 A 47 year old Chinese woman with poor English and bilateral tinnitus only experienced 50% RI for 30 minutes. Not considered therapeutic. She has normal hearing.

6.2 This 31 year old male had tinnitus that was louder at night and interfering with his sleep. He experienced 100% RI (i.e. no tinnitus) in the left ear for 12 hours and 50% RI in the right ear for 12 hours. His response was sufficient to allow undisturbed sleep. His audiogram shows normal hearing.

6.3 This 49 year old woman had a profound hearing loss in the right ear and 50 dB hearing loss in the left ear due to chronic middle ear disease. She achieved 100% RI for 12 hours but experienced rebound RI lasting 6 hours and then the tinnitus returned to its usual level.

6.4 This 59 year old Chinese volunteer had very poor English. He had bilateral tinnitus with a bilateral high tone sensorineural loss. This volunteer was very difficult to assess due to language problems. He had 60% RI but could not be contacted for follow up. Considered a non-responder.

6.5 A 78 year old male with a small high tone sensorineural loss and a mastoid cavity in the left ear from previous surgery. The tinnitus was in the right ear and had been present for 6 years. He experienced 100% RI for 4 hours which then became 50% for an additional 8 hours. Considered a therapeutic response.

6.6 A 44 year old male with a high tone sensorineural loss. His tinnitus was masked by the signal but he did not experience RI.

6.7 A 55 year old woman with a bilateral 40 dB sensorineural loss. The tinnitus was easily masked but she did not experience RI.

6.8 A 58 year old woman with bilateral tinnitus of 8 years duration and a normal audiogram. She experienced 80% RI which lasted 8 hours. Her tinnitus returned when she was exposed to the noise of a loud cocktail party.

6.9 This volunteer is a 63 year old farmer. His tinnitus was so severe that he was considering suicide. However he had no psychiatric illness. He had a bilateral high tone sensorineural loss due to noise exposure and presbyacusis. His initial response was 80% RI for 7 hours. Due to this good response he was treated daily for 4 days. On the $4^{th}$ day he experienced 100% RI (no tinnitus) and was reduced to tears by the relief of his tinnitus.

6.10 A 66 year old male with bilateral high tone sensorineural loss due to presbyacusis. He had undergone tinnitus reduction therapy (TRT) monthly for 1 year at a hospital and had been fitted with a white noise masker but had no RI with the white noise generator. With the XYXZ signal he experienced 100% RI right ear for 12 hours and 60% RI left ear for 12 hours. On a second application he had 70% RI right ear for 24 hours and 30% RI left ear for 24 hours.

6.11 A 61 year old male with a moderately severe bilateral high tone sensorineural loss due to industrial noise and presbyacusis. He wears bilateral hearing aids and had been tested with signals that were the forerunner of XYXZ without good effect. With XYXZ he experienced 60% RI right ear for 4 hours and 70% RI left ear for 4 hours.

6.12 A 61 year old male with a small sensorineural of 20-40 dB only at 3 KHz and 4 KHz and normal at other frequencies and bilateral tinnitus. He experienced 80% RI in both ears but it only lasted 1 hour. Not considered a therapeutic response due to the short duration of RI but could respond to serial exposure.

6.13 A 45 year old male with unremitting bilateral tinnitus interfering with his sleep. His audiogram shows a 50 dB sensorineural loss at all frequencies and a left high tone sensorineural loss. He experienced 70% RI in both ears for 4 hours.

6.14 A 49 year old male with a moderately severe high tone sensorineural loss due to noise exposure and bilateral tinnitus. His reporting was inconsistent. He initially reported 100% RI but when telephoned by the inventor the next day said he only had 50% RI for 1 hour. Thus this volunteer is not considered a therapeutic response.

6.15 A 47 year old female with a left 30 dB sensorineural loss of unknown cause and left tinnitus. The right ear was normal. She experienced 50% RI lasting 7 hours.

6.16 A 42 year old male with a 20-40 dB high tone loss at only 3 KHz and 4 KHz due to noise. He experienced no RI.

6.17 A 47 year old male with a 50 dB loss in the left ear at 3 KHz and 4 KHz due to an injury. He had left tinnitus. The right ear was normal. He experienced 60% RI but could not be contacted for follow up.

6.18 A 59 year old male with left tinnitus and a normal audiogram. He did not experience RI.

6.19 A 35 year old female professional musician with a 30 dB dip in her hearing at 6 KHz in both ears but normal hearing at other frequencies. She had bilateral hissing tinnitus that had been present for 19 years. She had 100% RI in both ears lasting 24 hours. This was the first time in her adult life that her tinnitus has stopped and she was very excited about the prospect of being able to switch her tinnitus off at will.

These examples show successful alleviation or treatment of the symptoms of tinnitus in many of the above sufferers. Moreover, whilst the efficacy of the treatment is not predictable or explicable in the context of the current knowledge and theory of auditory function, the relief experienced by the treated tinnitus sufferers is profound.

Although the physiological basis for the above results which have been achieved is not known, there is a clear distinction in the results achieved with the above described non-sinusoidal pulsating electric waveforms and those results achieved by others previously using pure tones and/or white noise, both of which are purely sinusoidal. It is possible that the physiological basis is due to the intermittent stimulation or the intermittent application of energy to those portions of the sufferer's anatomy which are actually causing the symptoms of tinnitus.

To summarize, there is disclosed an internet based system for the acoustic treatment of tinnitus, the system comprising a website hosted by an internet service provider, a payment acceptance facility associated with the website, and an acoustic signal associated with the website, wherein a sufferer of tinnitus can access the website via the internet, provide an accepted payment and download the acoustic signal to a headphone or a like acoustic transducer and associated with at least one ear of said sufferer and wherein the acoustic signal comprises a non-sinusoidal pulsating electric waveform having a pulse repetition rate less than 100 Hz.

There is also disclosed a method of treatment of tinnitus, said method comprising the steps of:
(i) applying a headphone or like acoustic transducer to at least one ear of a tinnitus sufferer, and
(ii) applying an acoustic signal to the headphone, wherein the acoustic signal comprises a non-sinusoidal pulsating electric waveform having a pulse repetition rate less than 100 Hz.

Further, there is disclosed an electrical generator for the treatment of tinnitus, the generator comprising at least one oscillator means to generate a non-sinusoid pulsating electric waveform having a pulse repletion rate no greater than 100 Hz, and an output connection adapted to connect with a headphone or like acoustic transducer.

Also disclosed is an electrical playback device for the treatment of tinnitus, the device comprising an electronic or magnetic storage means in which is stored a non-sinusoidal pulsating electric waveform having a pulse repetition rate less than 100 Hz, and an output connection adapted to connect with a headphone or like acoustic transducer.

Similarly disclosed is a stored audio product for the treatment of tinnitus, the product comprising an electric or magnetic storage means in which is stored a non-sinusoidal pulsating electric waveform having a pulse repletion rate less than 100 Hz, the product when actuated in a compatible electrical playback device reproducing the waveform in a form acceptable to a headphone or like acoustic transducer.

Additionally disclosed is a cochlear implant including a processor unit and an implantable electrode connected to the processor unit to receive a voltage therefrom, the processor unit being programmed to receive or generate a non-sinusoidal pulsating electric waveform having a pulse repetition rate less than 100 Hz which is applied to the implantable electrode.

Preferably the pulsating electric waveform is selected from the group consisting of square waves, triangle waves, and sawtooth waves.

Preferably the pulsating electric waveform comprises a sequence of three of the waves each of a predetermined duration.

Preferably the sequence comprises a first square wave, followed by a triangular wave, followed by a second square wave.

Preferably the first and second square waves are different.

Preferably, each of the durations is in the range from approximately one minute to approximately 20 minutes.

Preferably each of the waves of the sequence is separated in time by a corresponding pause period.

Preferably, each of the pause periods is in the range of from approximately zero to approximately 5 minutes.

For some sufferers, the sufferer of tinnitus preferably has his or her head substantially inverted during application of the non-sinusoidal pulsating electric waveform to the headphone or like acoustic transducer associated with at least one ear of said sufferer.

Preferably the pulse repetition rate is between approximately 20 Hz and approximately 40 Hz. Most preferably, the pulse repetition rate is approximately 30 Hz.

Preferably, the acoustic output delivered from the acoustic signal is increased to a level at which a masking effect is first achieved in the tinnitus sufferer.

The foregoing describes only some embodiment(s) of the present invention and modifications, obvious to those skilled in the medical technology arts, can be made thereto without departing from the scope of the present invention.

The term "comprising" (and its grammatical variations) as used herein is used in the inclusive sense of "including" or "having" and not in the exclusive sense of "consisting only of".

While the principles of the invention have been described above in connection with preferred embodiments, it is to be clearly understood that this description is made only by way of example and not as a limitation of the scope of the invention.

The invention claimed is:

1. A method of treatment of tinnitus, said method comprising the steps of:
applying an acoustic transducer to at least one ear of a tinnitus sufferer having tinnitus symptoms;
applying only an acoustic signal to said acoustic transducer so that said acoustic signal is delivered to said at least one ear of said tinnitus sufferer, said acoustic signal being without any white noise, ultrasonic component, ultrasonic carrier, radio frequency waves or radio frequency carrier, and said acoustic signal comprising a non-sinusoidal pulsating electric waveform having a pulse repetition rate less than 100 Hz;

removing said acoustic transducer and said acoustic signal from said at least one ear of said tinnitus sufferer.

2. The method as claimed in claim 1, wherein said pulse repetition rate is between approximately 10 Hz and approximately 80 Hz.

3. The method as claimed in claim 2, wherein said pulse repetition rate is between approximately 20 Hz and approximately 40 Hz.

4. The invention as claimed in claim 3, wherein said pulse repetition rate is approximately 30 Hz.

5. The method as claimed in claim 1, wherein said non-sinusoidal pulsating electric waveform comprises a plurality of waves selected from the group consisting of square waves, triangle waves, and sawtooth waves.

6. The method as claimed in claim 5, wherein said pulsating electric waveform comprises a sequence of three of said plurality of waves, each of a predetermined duration.

7. The method as claimed in claim 6, wherein said sequence comprises a first square wave, followed by a triangular wave, followed by a second square wave.

8. The method as claimed in claim 7, wherein said first square wave is different from the second square wave.

9. The method as claimed in claim 6, wherein each of said predetermined durations is in the range of approximately one minute to approximately 20 minutes.

10. The method as claimed in claim 6, wherein said step of applying only an acoustic signal to said acoustic transducer further comprises providing a pause period between each of said plurality of waves during which no acoustic signal is applied to the acoustic transducer.

11. The method as claimed in claim 10, wherein said pause period has a duration equal to or less than approximately 5 minutes.

12. The method as claimed in claim 1, further comprising positioning a head of the tinnitus sufferer in a substantially inverted position during at least a portion of said step of applying only an acoustic signal to said acoustic transducer.

13. The method as claimed in claim 1, wherein the step of applying an acoustic transducer to at least one ear of a tinnitus sufferer comprises applying an acoustic transducer to both ears of a tinnitus sufferer.

14. A method for treating tinnitus, comprising:

placing at least one acoustic transducer against an ear, in the ear or against a head of a human being having tinnitus symptoms;

supplying only at least one acoustic signal to each of the at least one acoustic transducers so that said at least one acoustic signal is delivered to said human being having tinnitus symptoms, each of the at least one acoustic signals being without any white noise, ultrasonic component, ultrasonic carrier, radiofrequency waves or radio frequency carrier, and consisting of a non-sinusoidal pulsating electric waveform having a pulse repetition rate less than 100 Hz;

removing said at least one acoustic signal from each of the at least one acoustic transducers, resulting in residual inhibition of said tinnitus symptoms by at least 50% in intensity for a period of at least three hours after said at least one acoustic signal has been removed from each of said at least one acoustic transducers.

15. The method as claimed in claim 14, wherein the supplying step comprises supplying a plurality of acoustic signals to each of the at least one acoustic transducers, each of the plurality of acoustic signals consisting of a non-sinusoidal pulsating waveform having a pulse repetition rate between 10 Hz and 100 Hz.

16. The method of claim 15, further comprising providing a pause period between each of the plurality of acoustic signals during which no acoustic signal is supplied to the acoustic transducer.

17. The method as claimed in claim 15, wherein each of the plurality of acoustic signals consists of a non-sinusoidal pulsating waveform selected from the group consisting of square waves, triangle waves, and sawtooth waves.

18. The method as claimed in claim 15, wherein said plurality of acoustic signals consists of a first square wave, followed by a triangular wave, followed by a second square wave.

19. The method as claimed in claim 18, wherein said first square wave is different from the second square wave.

\* \* \* \* \*